United States Patent
Lee et al.

(10) Patent No.: US 9,237,871 B2
(45) Date of Patent: Jan. 19, 2016

(54) X-RAY IMAGING APPARATUS, X-RAY DETECTION DEVICE, AND X-RAY IMAGE GENERATION METHOD

(71) Applicant: SAMSUNG ELECTRONICS CO., LTD., Suwon-si (KR)

(72) Inventors: Kang Eui Lee, Seoul (KR); Jong Ha Lee, Hwaseong-si (KR); Kwang Eun Jang, Busan (KR); Young Hun Sung, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 284 days.

(21) Appl. No.: 14/045,924

(22) Filed: Oct. 4, 2013

(65) Prior Publication Data

US 2014/0185748 A1 Jul. 3, 2014

(30) Foreign Application Priority Data

Dec. 28, 2012 (KR) .................. 10-2012-0156719

(51) Int. Cl.
*A61B 6/00* (2006.01)
*A61B 6/02* (2006.01)

(52) U.S. Cl.
CPC ............... *A61B 6/022* (2013.01); *A61B 6/025* (2013.01); *A61B 6/4241* (2013.01); *A61B 6/461* (2013.01); *A61B 6/482* (2013.01); *A61B 6/5205* (2013.01); *A61B 6/5223* (2013.01)

(58) Field of Classification Search
CPC ...... A61B 6/022; A61B 6/025; A61B 6/4241; A61B 6/461; A61B 6/482; A61B 6/5205; A61B 6/032
USPC ................................................. 378/21, 37
See application file for complete search history.

(56) References Cited

U.S. PATENT DOCUMENTS

| 7,751,528 | B2 | 7/2010 | Zhou et al. |
| 7,940,885 | B2 | 5/2011 | Stanton et al. |
| 2008/0267484 | A1* | 10/2008 | Chen ..................... A61B 6/032 382/132 |

FOREIGN PATENT DOCUMENTS

| KR | 10-1043331 B1 | 6/2011 |
| KR | 10-2011-0127444 A | 11/2011 |

* cited by examiner

*Primary Examiner* — Courtney Thomas
(74) *Attorney, Agent, or Firm* — Sughrue Mion, PLLC

(57) ABSTRACT

An X-ray imaging apparatus includes an X-ray emitter that emits X-rays to an object at a plurality of positions; a detector that detects X-rays having passed through the object and converts the detected X-rays into electric signals; and an image processor that is configured to generate X-ray images at the plurality of positions by reading out the electric signals, acquire volume data of the object using the X-ray images, and reproject the acquired volume data by using different bands of energy spectrums to acquire reconstructed reprojection images of different energy bands.

17 Claims, 15 Drawing Sheets

X-RAY IMAGING APPARATUS, X-RAY DETECTION DEVICE, AND X-RAY IMAGE GENERATION METHOD

CROSS-REFERENCE TO RELATED APPLICATION

This application claims priority from Korean Patent Application No. 10-2012-0156719, filed on Dec. 28, 2012 in the Korean Intellectual Property Office, the disclosure of which is incorporated herein by reference in its entirety.

BACKGROUND

1. Field

Apparatuses and methods consistent with exemplary embodiments relate to an X-ray imaging apparatus, an X-ray detection device, and an X-ray image generation method.

2. Description of the Related Art

X-rays directed to a particular material may pass through the material, or may be absorbed at a predetermined rate by the material to thereby be attenuated according to physical properties of tissues, structures, or materials inside an object. An X-ray imaging apparatus is devised to acquire an image of tissues, structures or materials inside an object using transmission or absorption/attenuation properties of X-rays with respect to a particular material.

More specifically, an X-ray imaging apparatus emits X-rays to an object, senses X-rays having passed through the object or directed around the object, and generates an X-ray image of tissues, structures or materials inside the object based on the sensed X-rays. Since the X-ray imaging apparatus provides an image of the tissues or structures inside the object as described above, a doctor may utilize the X-ray imaging apparatus to detect any diseases or other abnormalities of a human body. Additionally, the X-ray imaging apparatus may be used to observe internal structures of objects or components, and may be used as a scanner to scan luggage in the airport, etc.

Examples of the X-ray imaging apparatus include a general X-ray imaging apparatus, a Computed Tomography (CT) or Full Field Digital Mammography (FFDM) apparatus.

An FFDM apparatus is an X-ray imaging apparatus that captures an image of the female breast and detects defects, such as cancer tissues. In operation, the FFDM apparatus emits X-rays to a breast placed on a support plate from the top of the breast, and acquires an X-ray image of the breast by detecting X-rays having passed through the breast. More specifically, if an X-ray emitter located above the horizontal support plate emits X-rays to the breast placed on the support plate after the breast is compressed using a compressor, an X-ray detector located below the support plate senses X-rays having passed through the breast, thereby generating a planar X-ray image that shows tissues inside the breast.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide an X-ray imaging apparatus and an X-ray image generation method, which may acquire a multi-energy X-ray image and a stereoscopic X-ray image with less X-ray exposure.

One or more of exemplary embodiments may generate a multi-energy X-ray image and a stereoscopic X-ray image, which represent an enhanced contrast between materials or internal tissues inside an object irradiated with X-rays.

One or more of exemplary embodiments may generate an X-ray image having high readability even if materials or tissues inside an object have similar X-ray attenuation factors.

In accordance with an aspect of an exemplary embodiment, an X-ray imaging apparatus includes an X-ray emitter that emits X-rays to an object at a plurality of positions, a detector that detects X-rays having passed through the object and changes the detected X-rays into electric signals, and an image processor that generates a plurality of X-ray images at a plurality of positions by reading out the electric signals, acquires volume data regarding the object using the plurality of X-ray images, and reprojects the acquired volume data using different energy spectrums to acquire reprojection images reconstructed on a per energy band basis. The image processor may generate at least one multi-energy X-ray (MEX) image using the plurality of acquired reprojection images.

In accordance with another aspect of an exemplary embodiment, an X-ray imaging apparatus includes an X-ray emitter that emits X-rays to an object at a plurality of positions, a detector that detects X-rays having passed through the object and changes the detected X-rays into electric signals, and an image processor that generates a plurality of X-ray images at a plurality of positions by reading out the electric signals, acquires volume data regarding the object using the plurality of X-ray images, reprojects the acquired volume data at different positions to acquire a plurality of reprojection images captured at different positions, and controls generation of a stereoscopic image or display of a stereoscopic image based on at least two reprojection images among the plurality of reprojection images captured at the different positions. In this case, the image processor may generate a multi-energy X-ray image.

The image processor of the X-ray imaging apparatus may acquire a plurality of reprojection images by reprojecting the acquired volume data at different positions using different energy spectrums, and may generate a stereoscopic image using the plurality of reprojection images.

In accordance with another aspect of an exemplary embodiment, an X-ray imaging apparatus includes an X-ray emitter that emits X-rays to an object at a plurality of positions, a detector that detects X-rays having passed through the object and changes the detected X-rays into electric signals, and an image processor that generates a plurality of X-ray images at a plurality of positions by reading out the electric signals, generating a virtual object based on volume data after calculating the volume data regarding the object using the plurality of X-ray images, and acquiring virtual X-ray images of the virtual object reconstructed on a per energy band basis by virtually emitting X-rays having different energy spectrums to the generated virtual data.

In accordance with another aspect of an exemplary embodiment, an X-ray detection device includes a detector that detects X-rays having passed through an object and changes the detected X-rays into electric signals, and an image processor that generates a plurality of X-ray images at a plurality of positions by reading out the electric signals, acquires volume data regarding the object using the plurality of X-ray images, and reprojects the acquired volume data using different energy spectrums to acquire reprojection images reconstructed on a per energy band basis.

In accordance with an aspect of an exemplary embodiment, an X-ray image generation method includes emitting X-rays to an object at a plurality of positions plural times, detecting X-rays having passed through the object and changing the detected X-rays, emitted plural times, into electric signals, generating a plurality of X-ray images by reading out the respective electric signals, calculating volume data regarding the object using the plurality of X-ray images, reprojecting the acquired volume data using different energy spectrums, and acquiring reprojection images reconstructed on a per energy band basis.

BRIEF DESCRIPTION OF THE DRAWINGS

The above and/or other aspects will become more apparent by describing certain exemplary embodiments, with reference to the accompanying drawings, in which.

DETAILED DESCRIPTION

Figure 1:
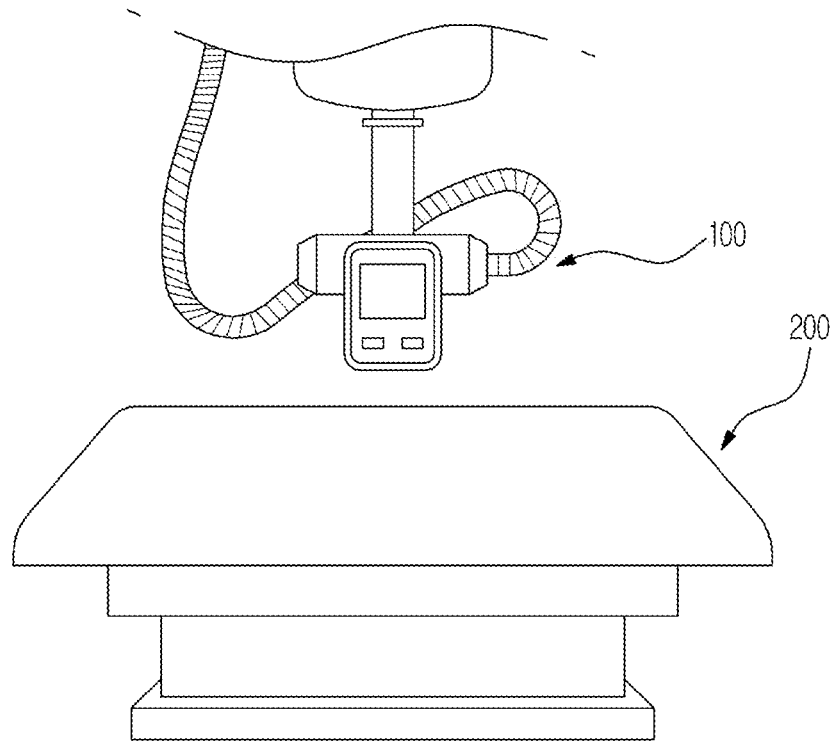
FIG. 1 is a perspective view illustrating an exemplary embodiment of an X-ray imaging apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

Hereinafter, an X-ray imaging apparatus according to the exemplary embodiments will be described with reference to FIGS. 1 to 10.

In FIG. 1, according to an exemplary embodiment of the X-ray imaging apparatus, a Digital Radiography (DR) system is illustrated, in which an X-ray detection device 200 takes the form of a table such that an object 230 is placed on the X-ray detection device 200 and is irradiated with X-rays emitted from the top of the X-ray detection device 200.

Figure 2:
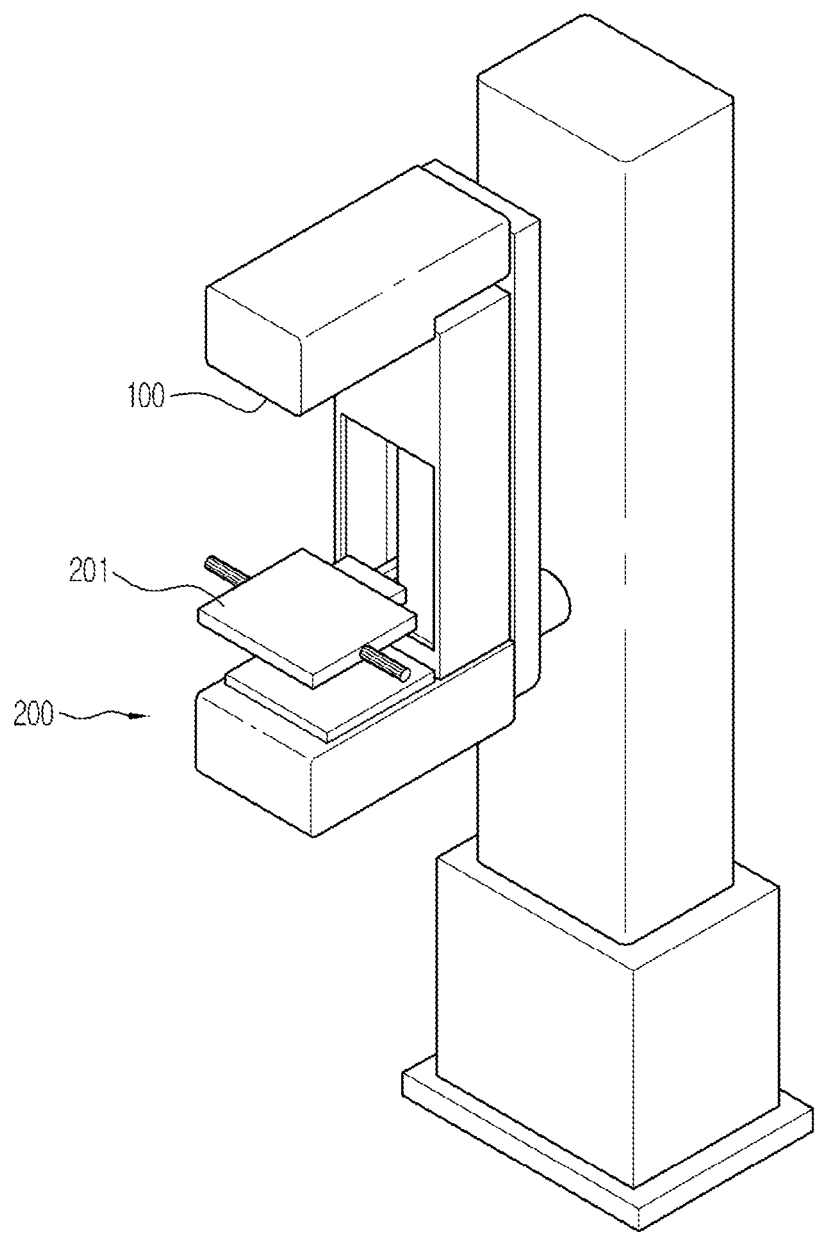
FIG. 2 is a perspective view illustrating an exemplary embodiment of a Full Field Digital Mammography (FFDM) apparatus.

In FIG. 2, according to an exemplary embodiment of the X-ray imaging apparatus, a Full Field Digital Mammography (FFDM) apparatus is illustrated, in which an X-ray emission device 100 is installed in an upper region, an X-ray detection device provided with an X-ray detector, for example, an X-ray detection panel that detects X-rays having passed through a breast placed on an upper surface thereof is installed in a middle region, and a compressor 201 is installed above the X-ray detection device 200 to compress the breast via vertical movement thereof.

However, the exemplary embodiments are not limited to the DR system and the FFDM apparatus as illustrated in FIGS. 1 and 2, and may be applied to other types of X-ray imaging apparatuses, for example, a Computed Tomography (CT) apparatus, that may acquire an X-ray image of the interior of an object by emitting X-rays to the object.

Figure 3:
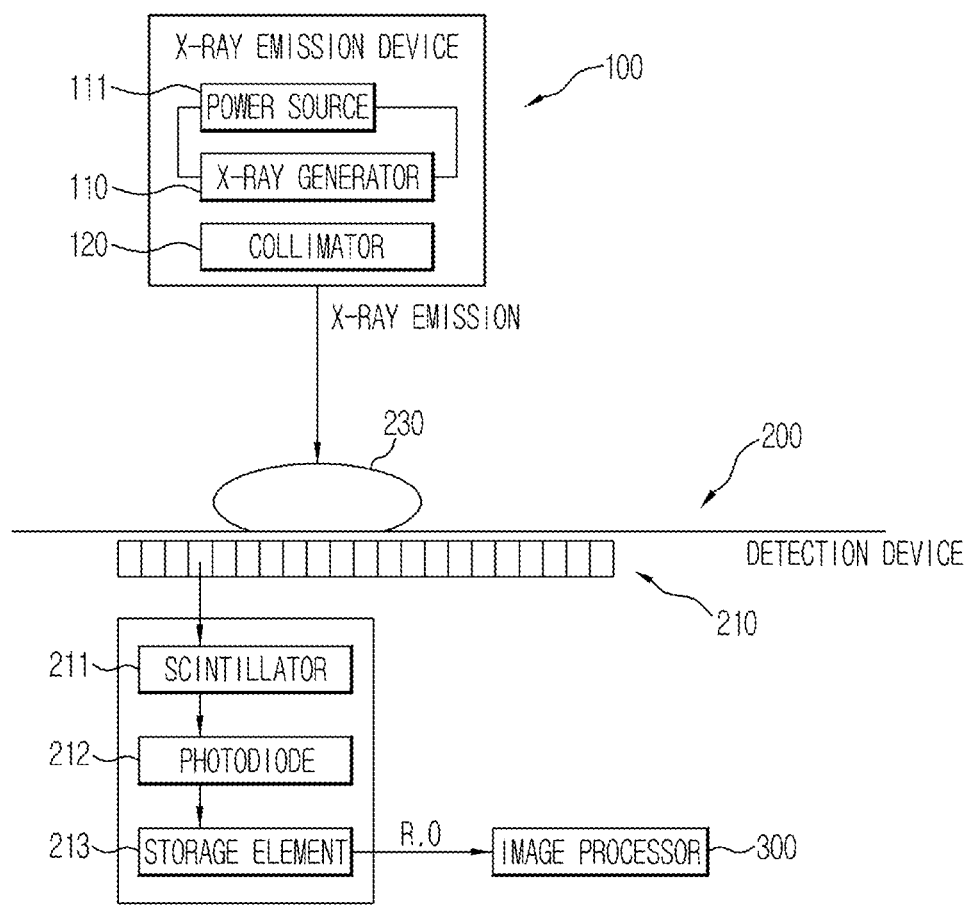
FIG. 3 is a view illustrating a configuration of the X-ray imaging apparatus according to an exemplary embodiment.

As illustrated in FIGS. 1 to 3, according to an exemplary embodiment, the X-ray imaging apparatus includes the X-ray emission device 100 that generates X-rays and emits the generated X-rays to the object, and the X-ray detection device 200 that receives X-rays having passed through the object placed thereon or X-rays directed around the object.

More specifically, the X-ray emission device 100, as illustrated in FIG. 3, may include a power source 111 and an X-ray generator 110 electrically connected to the power source 111. The X-ray generator 110 may include an X-ray tube in which electrons are accelerated upon receiving a predetermined voltage from the power source 111 and radiation, e.g., X-rays is generated when the accelerated electrons are reduced in speed around an anode by Coulomb force.

In this case, power of X-rays generated by the X-ray generator 110, i.e., energy level is determined according to the voltage applied from the power source 111. More specifically, if low-voltage current is applied to both ends of the X-ray tube, electrons within the X-ray tube are accelerated to a relatively low speed, and low-energy X-rays are generated from the anode inside the X-ray tube. Conversely, if high-voltage current is applied to both ends of the X-ray tube, electrons within the X-ray are accelerated to a relatively high speed, and high-energy X-rays are generated from an anode.

Figure 4A:
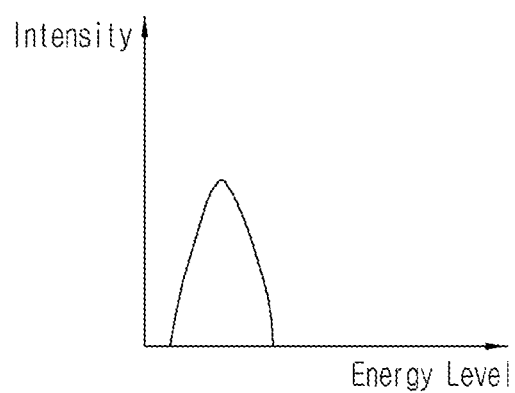
FIGS. 4A, 4B, and 4C are graphs illustrating different energy spectrums.
Figure 4B:
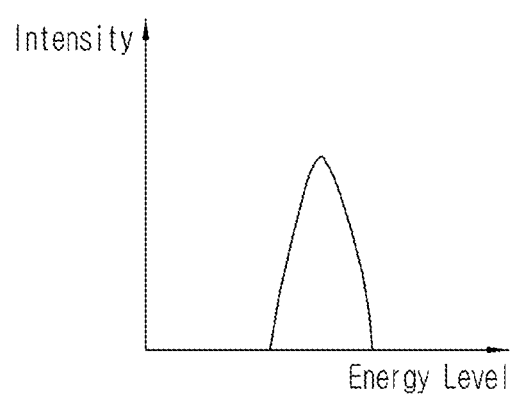
Figure 4C:
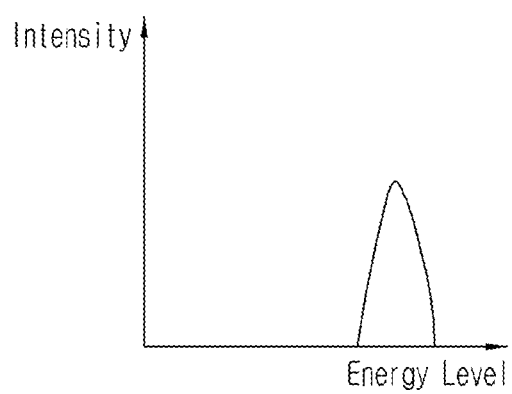

An energy spectrum of X-rays generated by the X-ray generator 110 may have various forms as illustrated in FIGS. 4A, 4B, and 4C according to a voltage applied thereto.

That is, if a low voltage is applied from the power source 111, X-rays having a low energy level energy spectrum $E_0$ as illustrated in FIG. 4A are generated. If a high voltage is applied, X-rays having a high energy level energy spectrum as illustrated in FIG. 4C are generated.

According to exemplary embodiments, X-rays generated by the X-ray generator 110 may pass through a collimator 120 prior to reaching the object. The collimator 120 serves as a guide device to control an X-ray emission direction or emission range. The collimator 120 may include a collimator filter or collimator blade formed of an X-ray absorbable material, for example, lead (Pb).

Figure 5:
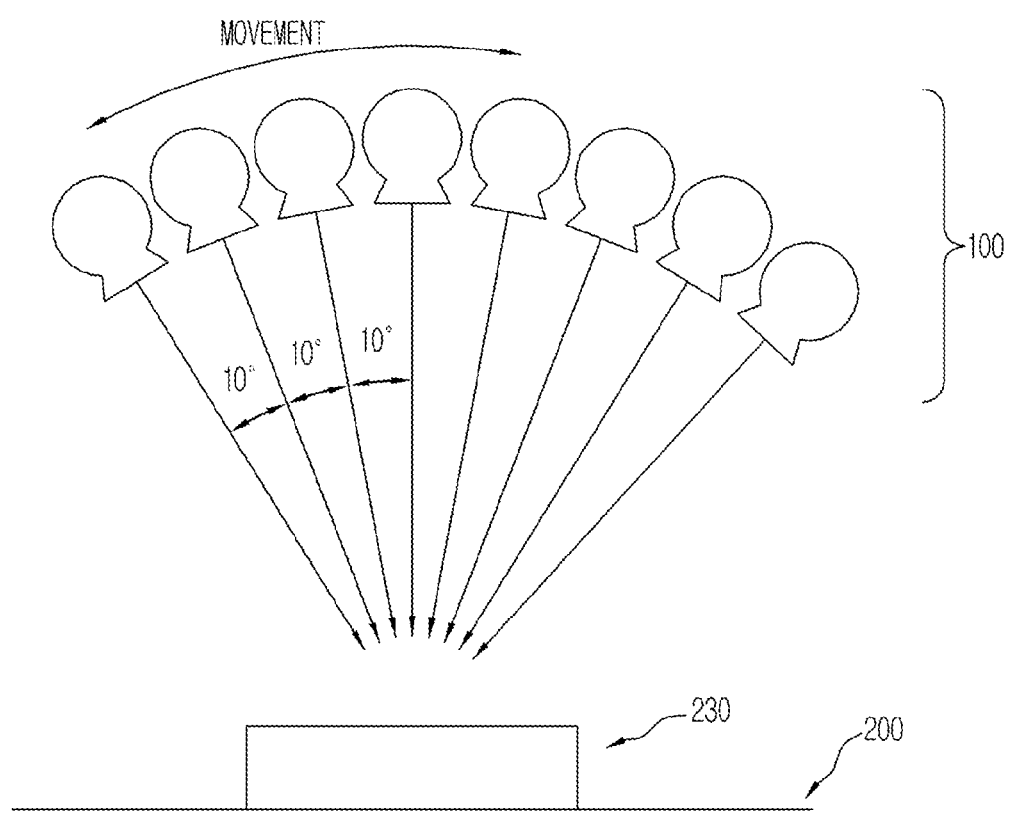
FIG. 5 is a view explaining an exemplary embodiment of an X-ray emission device that may emit X-rays at different positions.

According to an exemplary embodiment, the X-ray emission device 100, as illustrated in FIG. 5, is movable to emit X-rays to the object 230 at various positions. The X-ray emission device 100 may move only in a particular direction, for example, in a left-and-right direction of FIG. 5. Additionally, the X-ray emission device 100 may move along a predetermined arc-path about a given axis, for example, about a position of the object 230.

Figure 6:
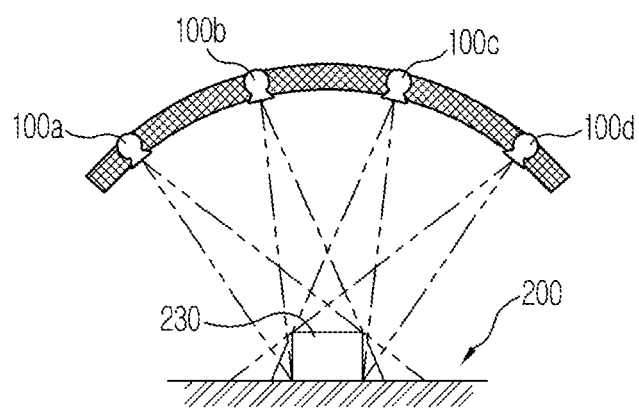
FIG. 6 is a view explaining an exemplary embodiment of an X-ray emission device that may emit X-rays at different positions.

According to an exemplary embodiment, the X-ray imaging apparatus, as illustrated in FIG. 6, may include a plurality of X-ray emission devices 100a, 100b, 100c, and 100d installed at different positions. The respective X-ray emission devices 100a to 100d may emit X-rays to the object 230 at installation positions thereof. As the X-ray emission device 100 is installed to move to predetermined positions using external power as illustrated in FIG. 5 or the plurality of X-ray emission devices 100 is installed at a plurality of positions as illustrated in FIG. 6, X-rays may be emitted to the object 230 at the plurality of different positions. Accordingly, the X-ray imaging apparatus may acquire an X-ray image captured at different angles.

Once the X-rays generated by the X-ray emission device 100 are emitted to the object 230, such as a human body, the X-ray detector 210 of the X-ray detection device 200 receives X-rays not observed by a variety of materials inside the object 230 among the X-rays emitted to the object 230, i.e., X-rays having passed through the object, or X-rays directed around the object.

The X-ray detector 210, for example, may be an X-ray detection panel that may detect X-rays. The X-ray detector 210 changes received X-rays into electric signals, and stores the electric signals in a storage element.

As illustrated in FIG. 3, the X-ray detector 210 may be divided into a plurality of pixels 210, and the respective pixels 210 of the X-ray detector 210 may include a scintillator 211, a photodiode 212, and a storage element 213.

The scintillator 211 outputs visible light photons according to collision of X-rays having passed through the object 230. The photodiode 212 changes the visible light photons into electric signals, and the changed electric signals are stored in the storage element 213, for example, in a capacitor.

According to an exemplary embodiment of the X-ray imaging apparatus, an image processor 300 reads out the electric signals stored in the storage elements 213, thereby generating an X-ray image. The X-ray image generated by the image processor 300 is displayed to a user via a display device, such as a monitor. The user may check an image of tissues, structures, or materials inside the object.

The image processor 300 may be provided in the X-ray detection device 200 according to one embodiment, or may be provided in an external data processing device that is connected to the X-ray detection device 200 in a wired or wireless communication network according to an exemplary embodiment.

Figure 7:
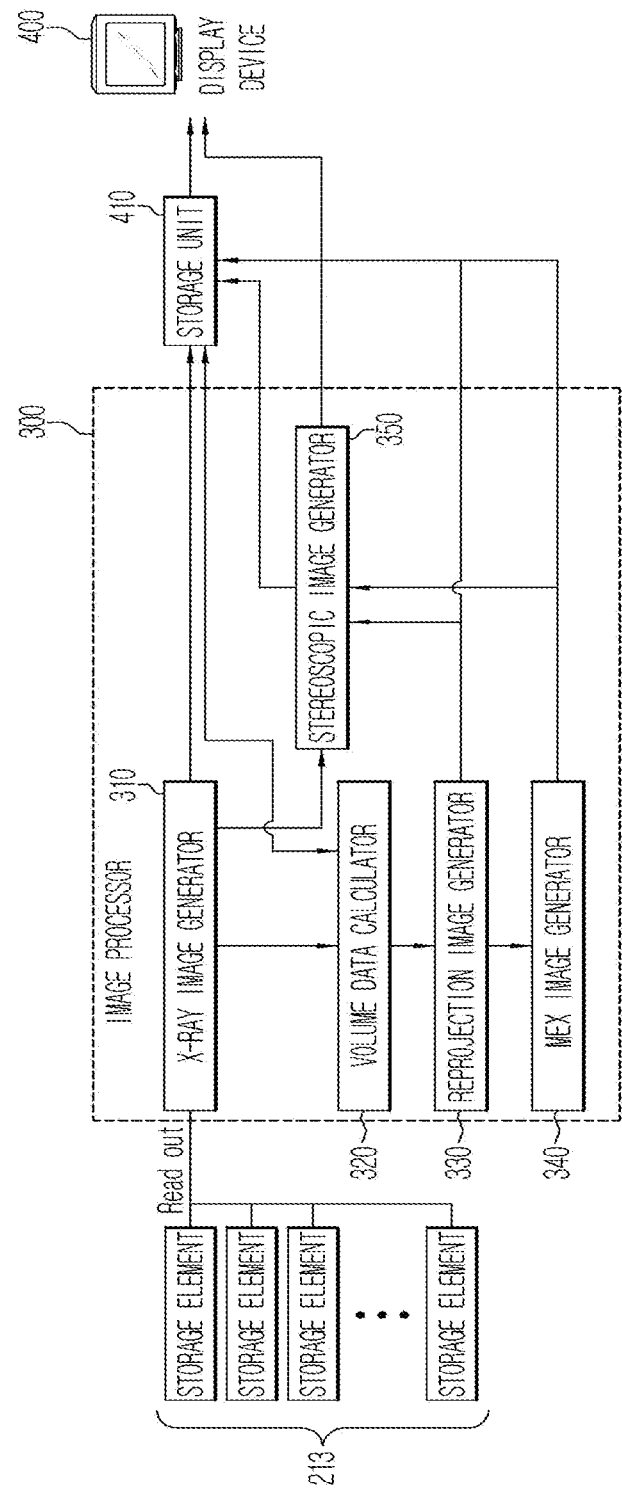
FIG. 7 is a view explaining an exemplary embodiment of an image processor included in the X-ray imaging apparatus.

As illustrated in FIG. 7, the image processor 300 according to an exemplary embodiment may include an X-ray image generator 310. The X-ray image generator 310 reads out the electric signals stored in the storage elements 213 of the respective pixels 210 of the X-ray detector 210, thereby generating an X-ray image from the readout electric signals. In this case, the respective pixels 210 of the X-ray detector 210 may correspond to respective pixels of a generated X-ray image.

The X-ray image generator 310 may generate a plurality of X-ray images corresponding to the number of X-ray emissions of the X-ray emission device 100, and the plurality of generated X-ray images is temporarily or semi-permanently stored in a separate storage unit 410. The image processor 300 may output a plurality of X-ray images stored in the storage unit 410 via an external display device 400, such as a monitor, etc.

According to an exemplary embodiment, the image processor 300 may further include a volume data calculator 320. The volume data calculator 320 acquires volume data of the object 230 using the plurality of X-ray images generated by the X-ray image generator 310.

Hereinafter, an exemplary embodiment of a method of calculating volume data by the volume data calculator 320 will be described.

Figure 8:
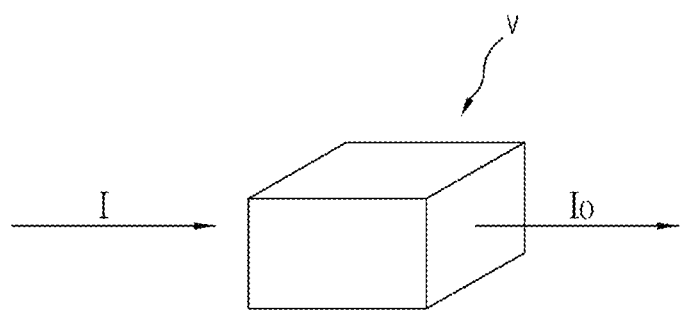
FIG. 8 is a view explaining energy of X-rays passing through a spatial volume element.

Referring to FIG. 8, when X-rays emitted from the X-ray emission device 100 pass through the object 230, the X-rays pass through any one spatial volume element (voxel) within the object 230. In this case, the X-rays emitted to the spatial volume element v are partially absorbed by a material within the spatial volume element, showing a change from an energy spectrum I to an energy spectrum $I_0$. Of course, in this case, it will be appreciated that in the case of a spatial volume element containing no material, such as a vacuum, the energy spectrum I undergoes no change. This is represented by the following Equation.

$$I_0 = I_e^{-x\mu}$$   Equation 1

Here, "$\mu$" denotes an attenuation factor or attenuation coefficient of X-ray energy determined according to a material within a spatial volume element v. "x" denotes an X-ray passage distance through a spatial volume element v, in other words, a thickness of the spatial volume element v.

Through use of "I" corresponding to an initial value of an energy spectrum of X-rays emitted by the X-ray emission device 100 and "$I_0$" corresponding to a detected result of the X-ray detector 210, calculation of the attenuation factor $\mu$ is possible. As such, data regarding the material in the spatial volume element v of the object 230 may be acquired.

Alternatively, to calculate volume data, the volume data calculator 320 may use known attenuation factors with regard to tissues inside the object, for example, bones, muscles, etc. In addition, to acquire an attenuation factor of one spatial volume element v, calculated attenuation factors of peripheral spatial volume elements v may be used. For example, the attenuation factor of one spatial volume element v may be estimated by calculating an average value of peripheral spatial volume elements v. Additionally, the attenuation factor of each spatial volume element v may be calculated under the assumption that spatial volume elements v within a predetermined region have the same attenuation factor.

Through the above-described method, data regarding a material within each spatial volume element v, i.e., each volume data may be acquired.

Synthesis of the acquired volume data enables reconstruction of the object 230 irradiated with X-rays. In this case, a reconstructed object may be equal to or very similar to the real object according to an X-ray irradiation method or a reconstruction method. In this case, the reconstructed object may be acquired in three-dimensionally.

The image processor 300 may further include a reprojection image generator 330.

The reprojection image generator 330, according to an exemplary embodiment, reprojects volume data of the object 230, acquired via the volume data calculator 320, using multiple different energy band spectrums, thereby generating a plurality of reprojection images that is reconstructed on a per energy band basis. For example, reprojection may be performed using different energy spectrums as illustrated in FIGS. 4A to 4C. In this case, energy spectrums for reprojection may be preset, or may be selected according to a user's need.

In particular, the reprojection image generator 330 generates a low energy-band reprojection image and a high energy-band reprojection, which may be used to enhance a contrast of X-ray reprojection images by an MEX image generator 340 that will be described hereinafter. This will be described later.

According to an exemplary embodiment, the reprojection image generator 330 may reproject volume data acquired via the volume data calculator 320 at a plurality of different positions, thereby generating a plurality of reprojection images captured at different positions Likewise, the reprojection positions may be preset, or may be selected according to a user's need. In this case, at least two positions of the plurality of reprojection positions may be close to each other, to assist a stereoscopic image generator 350 that will be described hereinafter in generating a stereoscopic image.

For example, as illustrated in FIG. 5, assuming that the Z-axis of the reconstructed object (the vertical axis) is 0 degrees, reprojection may be performed at positions having angles of 10 degrees, 20 degrees, and 30 degrees with respect to the Z-axis.

According to an exemplary embodiment, the reprojection image generator 330 performs reprojection at a plurality of different positions using multiple energy band spectrums, thereby acquiring a plurality of reprojection images reconstructed on a per energy band basis at different positions.

The image processor 300 may further include the MEX image generator 340.

The MEX image generator 340 generates at least one multi-energy X-ray image using the plurality of reprojection images generated by the reprojection image generator 330, more particularly, the plurality of reprojection images generated via reprojection using different energy spectrums.

If X-rays are emitted to the object, tissues having a high X-ray attenuation factor among tissues inside the object absorb a great quantity of emitted X-rays, which causes the X-ray detector 210 to detect only a small quantity of X-rays. Conversely, tissues having a low X-ray attenuation factor transmit a great quantity of X-rays, which causes the X-ray detector 210 to detect a great quantity of X-rays. Thus, tissues inside the object may be recognized according to the detected quantity of X-rays.

Figure 9:
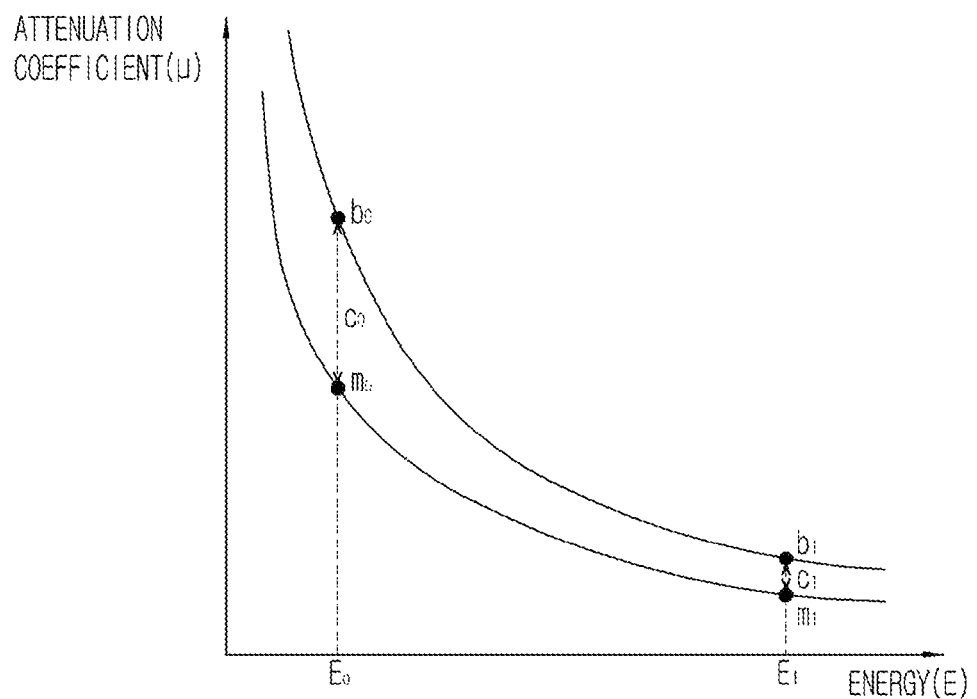
FIG. 9 is a graph illustrating a relationship between energy and an attenuation coefficient.

For example, as illustrated in FIG. 9, the X-ray attenuation factor varies according to the object 230, for example, tissues of a human body. That is, under emission of X-rays having the same energy spectrum, for example, $E_0$, bones have a greater attenuation factor $b_0$ than an attenuation factor $m_0$ of soft tissues, for example muscles. Thus, the detected quantity of X-rays varies according to an attenuation factor difference $c_0$, which enables discrimination of different tissues, for example, bones and muscles in an X-ray image.

Alternatively, the attenuation factor $\mu$ of a material inside the object varies according to the energy level of emitted X-rays.

Referring to FIG. 9, an X-ray energy band and an X-ray attenuation factor $\mu$ are inverse-proportional to each other. That is, as the energy band of X-rays emitted to the object 230 is increased, the attenuation factor $\mu$ is reduced, which increases the quantity of X-rays detected by the detector 210. Conversely, as the energy band of X-rays emitted to the object 230 is reduced, the attenuation factor $\mu$ is increased, which reduces the quantity of X-rays detected by the detector 210. In addition, an increase/reduction of the attenuation factor $\mu$ depending on an increase/reduction of the energy band may vary according to properties of materials.

Accordingly, if X-rays of a low energy band (see FIG. 4A and $E_0$ of FIG. 9) are emitted to the object, detection of soft tissues, such as muscles, blood vessels, breast, etc. may be possible due to a high attenuation factor of X-rays (in other words, high transmittance of X-rays through a material). Conversely, if high energy band X-rays (see FIG. 4C and $E_1$ of FIG. 9) are emitted to a human body, detection of hard tissues, such as bones, may be possible due to a low attenuation factor of X-rays (in other words, a low transmittance of X-rays through a material).

In other words, an acquirable X-ray image varies according to the energy spectrum of emitted X-rays as well as properties of tissues inside the object.

A multi-energy X-ray image utilizes characteristics that the attenuation factor of X-rays varies according to the energy level of X-rays. The multi-energy X-ray image is generated based on a plurality of different X-ray images acquired by emitting different energy spectrum X-rays to a single object 230 plural times.

The multi-energy X-ray image may be generated by overlapping or combining a plurality of different X-ray images acquired using different energy spectrum X-rays, or by adding a predetermined weight to each of a plurality of X-ray images and thereafter overlapping or combining the images. In addition, the multi-energy X-ray image may be acquired via energy subtraction between a plurality of X-ray images.

Accordingly, the multi-energy X-ray image enables inspection and verification of various tissues inside the object 230.

Referring to FIG. 9, if X-rays of low energy $E_0$ are emitted to two kinds of tissues, for examples, bones and muscles, the bones and the muscles have a relatively high difference $c_0$ in attenuation factors $b_0$ and $m_0$ thereof. Accordingly, a difference in the detected quantity of X-rays having passed through the bones and the muscles is increased, which may inevitably cause a great contrast. This provides clear discrimination between respective tissues. However, a signal-to-noise ratio (SNR) may be low due to the low X-ray energy. That is, great noise may be inevitable.

On the other hand, if X-rays of high energy $E_1$ are emitted to the object 230, two tissues, for examples, bones and muscles have a relatively low difference $c_1$ in the attenuation factors $b_1$ and $m_1$ thereof. Accordingly, a difference in the detected quantity of X-rays having passed through the bones and the muscles is reduced, which causes a reduced contrast. However, an SNR may be enhanced due to the high X-ray energy. That is, reduced noise may be accomplished.

The MEX image generator 340 may improve a contrast using a reprojection image of a low energy band $E_0$ and a reprojection image of a high energy band $E_1$ among a plurality of reprojection images generated by the above-described reprojection image generator 330.

As described above, a first reprojection image generated via reprojection using X-rays of a low-energy band $E_0$ has characteristics of a high contrast and a low SNR, whereas a second reprojection image generated via reprojection using X-rays of a high-energy band $E_1$ has characteristics of a low contrast and a high SNR. Accordingly, the MEX image generator 340 may enhance a contrast of the second reprojection image by, for example, adding a predetermined weight to the first reprojection image using data regarding the first reprojection image, for example, data regarding a boundary between the respective materials, thereby generating a multi-energy X-ray image having a high contrast and a high SNR.

The image processor 300 may further include a stereoscopic image processor 350.

The stereoscopic image processor 350 may control generation of a stereoscopic image using at least two X-ray images, or display of a stereoscopic image via the display device 400.

To control generation of a stereoscopic image or display of a stereoscopic image via the display device 400, the stereoscopic image processor 350 may use at least two X-ray images generated by the X-ray image generator 310, may use at least two X-ray images generated by the reprojection image generator 330, or may use at least two multi-energy X-ray images generated by the MEX image generator 340.

In general, since human eyes are spaced apart from each other by a distance of about 6 cm, images perceived by a left-eye and a right-eye are inevitably slightly different. Through such slight difference, e.g., a difference between the images perceived by the eyes, a human brain may recognize 3D-effects. A stereoscopic image is an image that allows a viewer to acquire 3D effects from images or video regenerated using binocular disparity caused by a distance between pupils of human eyes.

The stereoscopic image processor 350 may control display of a stereoscopic image via the display device 400 after generating the stereoscopic image by combining a plurality of images, i.e., a left-eye image and a right-eye image, or may individually output the left-eye image and the right-eye image via the display device 400 to allow the viewer to view a stereoscopic image.

According to an exemplary embodiment, the stereoscopic image processor 350 may allow the user to view X-ray images in a stereoscopic manner using Red-Cyan glasses. In this case, the stereoscopic image processor 350 performs red or cyan color correction on two adjacent multi-energy X-ray images among multi-energy X-ray images that have been generated by the MEX image generator 340 and subjected to reprojection at different positions. One of the two color-corrected multi-energy X-ray images is a left-eye image, and the other is a right-eye image. The stereoscopic image processor 350 overlaps two multi-energy X-ray images such that the overlapping images are displayed on one display device 400. In this case, the user may view the images displayed on the display device 400 in a stereoscopic manner using red-cyan glasses. Thus, the user, for example, a doctor or patient may stereoscopically view the reconstructed object.

According to an exemplary embodiment, the stereoscopic image processor 350 may use a polarized glasses method. The polarized glasses method is a method of displaying a left-eye image and a right-eye image in divided regions of a single screen. When using the polarized glasses method, the stereoscopic image processor 350, for example, selects two adjacent multi-energy X-ray images among multi-energy X-ray images generated by the MEX image generator 340. In this case, any one of the two multi-energy X-ray images is a left-eye image, and the other one is a right-eye image. Then, the stereoscopic image processor 350 may control generation of a stereoscopic image, or display of a stereoscopic image via the display device 400 by splitting the two multi-energy X-ray images, and thereafter coupling the split multi-energy X-ray images. When the user views the display device 400 through polarized glasses, the user may stereoscopically view an image of the reconstructed object.

According to an exemplary embodiment, the stereoscopic image processor 350 may use a shutter glasses method. The shutter glasses method is also referred to as a time-split method in which a left-eye image and a right-eye image are displayed on a screen at different times, thereby allowing the user to view a stereoscopic image. In this case, glasses worn by the user assist the left eye and the right eye of the user in perceiving only the left-eye image and the right-eye image respectively. The stereoscopic image processor 350, for example, selects two adjacent multi-energy X-ray images generated by the MEX image generator 340, and thereafter controls display of the two multi-energy X-ray images at different times on the display device 400, thereby allowing the user to view a stereoscopic image of the reconstructed object through the glasses.

Figure 10:
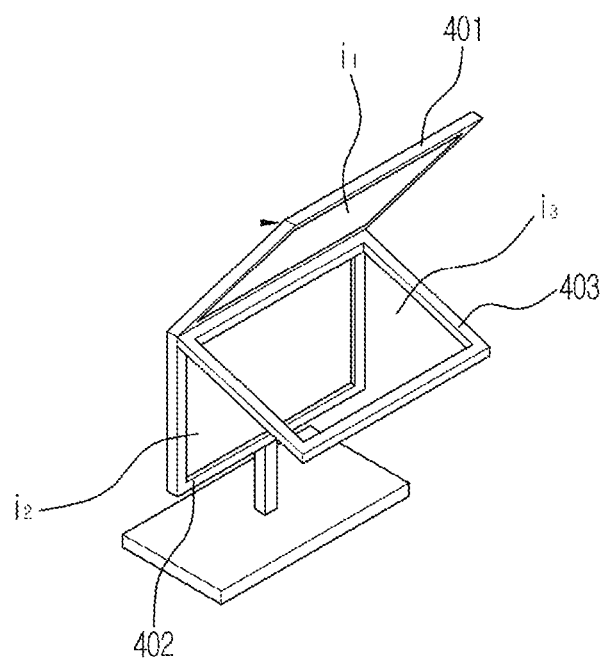
FIG. 10 is a perspective view illustrating an exemplary embodiment of a display device that displays a stereoscopic image in a half-mirror manner.

According to an exemplary embodiment, the stereoscopic image processor 350 may allow the user to view a stereoscopic image using a half-mirror method. When using the half-mirror method as illustrated in FIG. 10, the display device 400 includes first and second display units 401 and 402 that output different images $i_1$ and $i_2$, and a third display unit 403 that displays a stereoscopic image $i_3$. The stereoscopic image processor 350, for example, selects two adjacent multi-energy X-ray images generated by the MEX image generator 340 such that the respective multi-energy X-ray images are displayed on the first display unit 401 and the second display unit 402 respectively. Thereby, when the user views the third display unit 403 through stereoscopic glasses, the user may stereoscopically observe the reconstructed object by viewing a first X-ray image p1 and a second X-ray image p2 overlapping each other via the third display unit 403.

According to an exemplary embodiment, the X-ray imaging apparatus may allow the user to view a stereoscopic image via a non-glasses method using a lenticular sheet or a barrier plate. The stereoscopic image processor 350 may process images, or control display of an image of the reconstructed object via the display device 400, to allow the user to view a stereoscopic image using the non-glasses method.

According to an exemplary embodiment of the reprojection image generator 330 of the X-ray imaging apparatus, after the volume data calculator 320 calculates volume data regarding the object 230, the reprojection image generator 330 may perform virtual emission of X-rays to an object reconstructed based on the calculated volume data, i.e., a virtual object.

In this case, the reprojection image generator 330 may virtually emit X-rays having different energy spectrums, or may virtually emit X-rays at a plurality of different positions. In addition, the reprojection image generator 330 may virtually emit X-rays having multiple different energy spectrums at a plurality of different positions. Thereby, the reprojection image generator 330 may acquire virtual X-ray images of the virtual object, which are reconstructed on a per energy band basis, are captured at different positions, or are captured at different positions and then reconstructed on a per energy band basis.

In this case, the MEX image generator 340 may generate at least one virtual multi-energy X-ray image of the virtual object using the virtual X-ray images acquired via virtual emission of X-rays having multiple different energy spectrums. The generation of the virtual multi-energy X-ray image has been described above.

The stereoscopic image processor 350 may control generation of a stereoscopic image using the X-ray image, or display of a stereoscopic image via the display device 400 using X-ray images, virtual X-ray images or virtual multi-energy X-ray images generated by the X-ray image generator 310, the reprojection image generator 330, or the MEX image generator 340. The method of generating a stereoscopic image or displaying a stereoscopic image has been described above.

Hereinafter, an X-ray image generation method will be described with reference to FIGS. 11 to 13.

Figure 11:
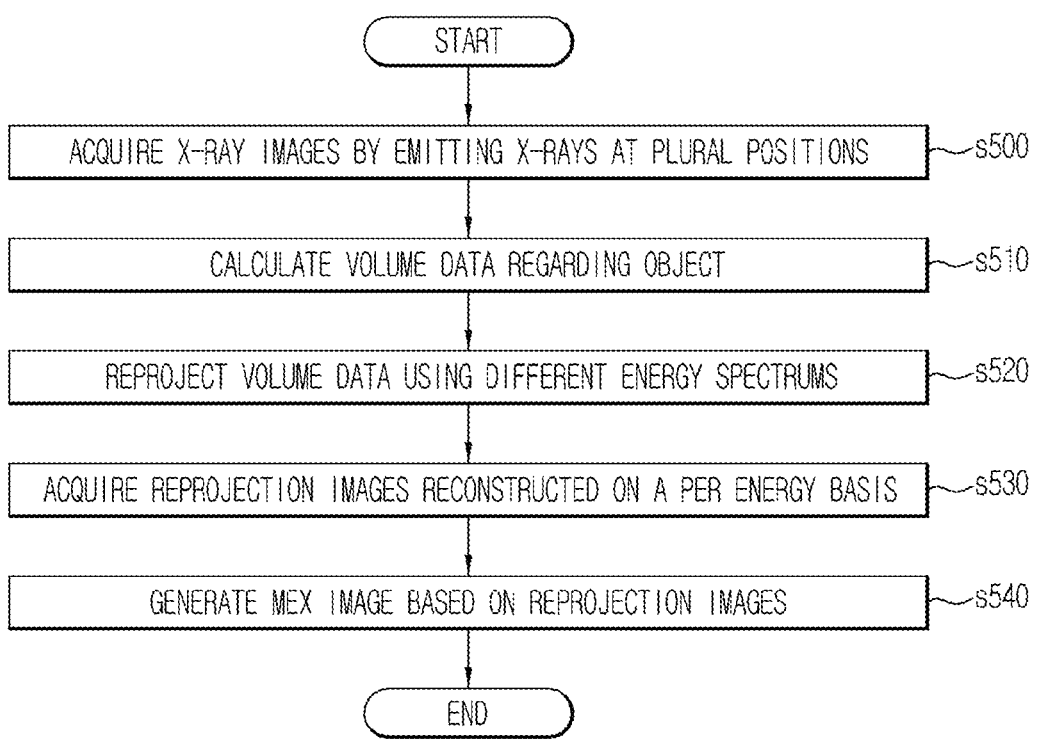
FIGS. 11, 12, and 13 are flowcharts illustrating various exemplary embodiments of an X-ray image generation method.

The X-ray image generation method, according to an exemplary embodiment, as illustrated in FIG. 11, includes acquiring a plurality of X-ray images by emitting X-rays to an object at a plurality of positions (operation s500).

Figure 12:
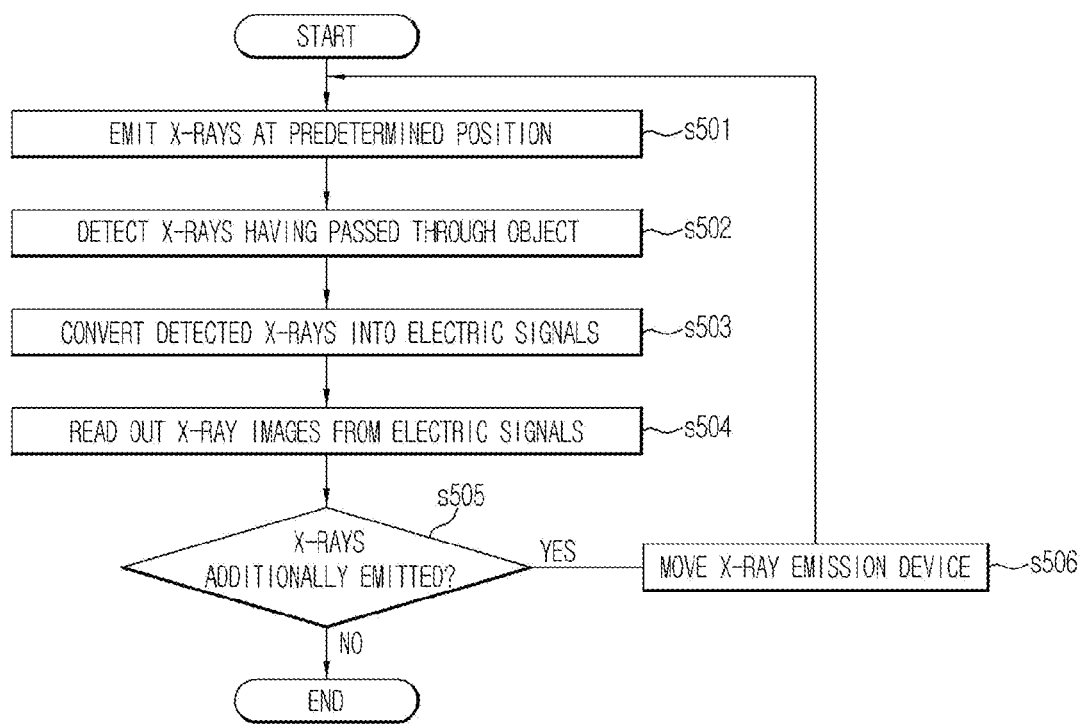

As illustrated in FIG. 12, to generate the plurality of X-ray images (operation s500), first, the X-ray emission device 100 emits X-rays to the object 230 at a predetermined position (operation s501), and the detector 210 of the X-ray detection device 200 detects X-rays having passed through the object or directed around the object (operation s502). The X-ray detector 210 changes the detected X-rays into electric signals using the scintillators 211 and the photodiodes 212, and stores the electric signals in the storage elements 213 (operation s503). Then, the image processor 300 reads out an X-ray image from the electric signals stored in the storage elements 213 (operation s504). If X-rays are additionally emitted to acquire an additional X-ray image (operation s505), according to an exemplary embodiment, the X-ray emission device 100 is moved to another X-ray emission position (operation s506). If the X-ray imaging apparatus includes a plurality of X-ray emission devices 100a to 100d, except for one X-ray emission device 100a that has already emitted X-rays, any one of the other X-ray emission devices 100b to 100d may emit X-rays to acquire an X-ray image at another position.

After acquiring the plurality of X-ray images (operation s500), the image processor 300 calculates volume data regarding the object 230 based on the plurality of acquired X-ray images (operation s510).

According to an exemplary embodiment of the X-ray image generation method, the attenuation factor of a spatial volume element v may be used for calculation of volume data. That is, calculation of the attenuation factor of the spatial volume element v may inform whether or not a material is present in the spatial volume element v or what material is present in the spatial volume element v. As such, the object 230 to which X-rays are emitted may be three-dimensionally reconstructed by synthesizing volume data acquired as described above.

The image processor 300 performs reprojection on the calculated volume data (operation s520).

In this case, the image processor 300 may perform reprojection using different energy spectrums (FIG. 4). That is, the image processor 300 calculates a reprojection image based on volume data, like acquisition of different energy band X-ray images by emitting multiple energy spectrum X-rays to the object, reconstructed based on the acquired volume data, plural times.

As a result, a plurality of reprojection images reconstructed on a per energy band basis is acquired (operation s530).

Then, the image processor 300 generates at least one multi-energy X-ray image (MEX image) using the plurality of acquired reprojection images (operation s540).

According to an exemplary embodiment, the multi-energy X-ray image may be acquired by adding a predetermined weight to each of the plurality of different energy spectrum X-ray images, and overlapping the images each other. In addition, the multi-energy X-ray image may be acquired by applying energy subtraction to any one of the plurality of different energy spectrum X-ray image, and applying the energy-subtracted image to any one of the other different energy spectrum X-ray images.

During generation of the multi-energy X-ray image, it may be possible to enhance a contrast between materials inside the object. As described above, a second reprojection image acquired via reprojection using high energy $E_1$ has a high SNR and low noise, but has difficulty in discriminating respective materials due to a low contrast between the materials. Accordingly, by performing MEX imaging using a first reprojection image acquired via reprojection using low energy $E_0$, it may be possible to enhance a contrast of the second reprojection image. In this way, a multi-energy X-ray image having a high contrast and high SNR may be acquired.

Figure 13:
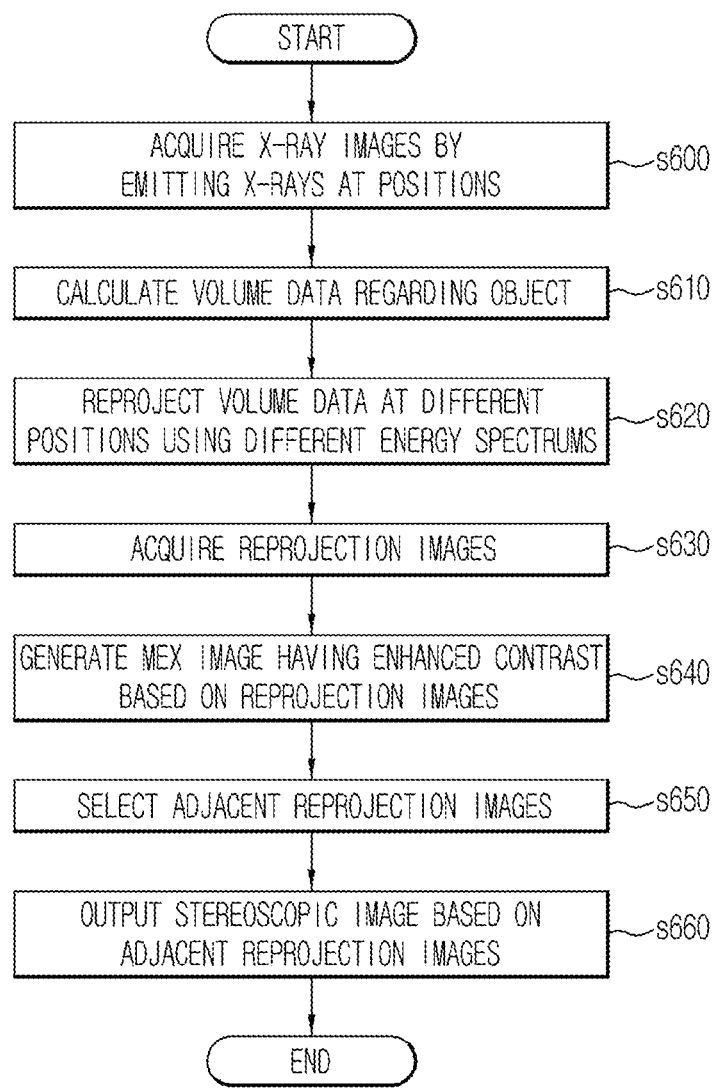

According to an exemplary embodiment, the X-ray image generation method, as illustrated in FIG. 13, includes acquiring a plurality of X-ray images of the object 230 by emitting X-rays to the object 230 at a plurality of positions (operation s600), and calculating volume data regarding the object 230 using the plurality of acquired X-ray images (operation s610).

The image processor 300 performs reprojection on the volume data at a plurality of different positions (operation s620). That is, the image processor 330 may calculate a reprojection image based on volume data, like acquisition of X-ray images captured at different positions by emitting X-rays to the object, reconstructed based on the acquired volume data, at a plurality of positions.

In this case, according to an exemplary embodiment, reprojection on the volume data may be performed plural times at the respective positions using multiple different energy spectrums.

As a result, a plurality of reprojection images is acquired (operation s630).

According to an exemplary embodiment, the image processor 300 may acquire multi-energy X-ray images having an enhanced contrast, similar to the above description, using a high-energy reprojection image and a low-energy reprojection image among the plurality of acquired reprojection images (operation s640).

The image processor 300 selects at least two reprojection images or multi-energy X-ray images among the plurality of acquired reprojection images or the multi-energy X-ray images having an enhanced contrast, according to an input stereoscopic image display instruction or without receiving an instruction (operation s650).

The image processor 300 may control generation of a stereoscopic image using a pair of the selected at least two reprojection images or multi-energy X-ray images, in other words, utilizing any one of the two images as a left-eye image and the other image as a right eye image, or may control output of the at least two reprojection images or multi-energy X-ray images on the display device 400, thereby allowing the user to view a stereoscopic image of the reconstructed object.

As is apparent from the above description, through provision of an X-ray imaging apparatus and an X-ray image generation method, a multi-energy X-ray image and a stereoscopic X-ray image may be acquired by emitting an absolutely or relatively small quantity of X-rays to an object, e.g., a human body. Accordingly, it may be possible to reduce object X-ray exposure.

Further, according to the exemplary embodiments, it may be possible to acquire an X-ray image having an enhanced contrast between materials inside the object irradiated with X-rays.

In particular, even if materials or tissues inside the object have similar attenuation factors, and discrimination therebetween is difficult, an X-ray image having high readability may be generated.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:
1. An X-ray imaging apparatus comprising:
an X-ray emitter that emits X-rays to an object at a plurality of positions;
a detector that detects X-rays having passed through the object and converts the detected X-rays into electric signals; and
an image processor that is configured to generate X-ray images at the plurality of positions by reading out the electric signals, acquire volume data of the object using the X-ray images, and reproject the acquired volume data by using different bands of energy spectrums to acquire reconstructed reprojection images of different energy bands.

2. The apparatus according to claim 1, wherein the image processor generates a multi-energy X-ray (MEX) image using the acquired reprojection images.

3. The apparatus according to claim 2, wherein the image processor generates the MEX image having an enhanced contrast between materials inside the object by using the reprojection images of the different energy bands.

4. The apparatus according to claim 3, wherein the image processor acquires the reprojection images captured at different positions by reprojecting the acquired volume data at the different positions.

5. The apparatus according to claim 4, wherein the image processor controls a generation of a stereoscopic image or a display of a stereoscopic image based on at least two reprojection images of the reprojection images captured at the different positions.

6. The apparatus according to claim 1, wherein the image processor reprojects the acquired volume data at different positions to acquire the reprojection images captured at the different positions, and controls a generation of a stereoscopic image or a display of a stereoscopic image based on at least two reprojection images of the reprojection images captured at the different positions.

7. The apparatus according to claim 6, wherein the image processor generates at least one multi-energy X-ray (MEX) image by using the acquired reprojection images.

8. The apparatus according to claim 7, wherein the image processor generates the MEX image having an enhanced contrast between materials inside the object by using the reprojection images of the different energy bands.

9. An X-ray image generation method comprising:
emitting X-rays to an object at a plurality of positions a plurality of times;
detecting X-rays having passed through the object and converting the detected X-rays, emitted the plurality of times, into electric signals;
generating X-ray images by reading out respective electric signals;
calculating volume data of the object by using the X-ray images;
reprojecting the volume data by using different bands of energy spectrums; and
acquiring reprojection images of different energy bands.

10. The method according to claim 9, further comprising generating a multi-energy X-ray (MEX) image by using the acquired reprojection images.

11. The method according to claim 10, wherein the generating the MEX image includes generating the MEX image having an enhanced contrast between materials inside the object by using the acquired reprojection images.

12. The method according to claim 9, wherein the reprojecting includes reprojecting the volume data at different positions by using the different bands of energy spectrums, and
the acquiring the reprojection images includes acquiring the reprojection images that are reconstructed on a per energy band basis and captured at the different positions.

13. The method according to claim 12, further comprising generating or displaying a stereoscopic image based on at least two reprojection images of the reprojection images captured at the different positions.

14. An X-ray imaging apparatus comprising:
an X-ray emitter that emits X-rays to an object at a plurality of positions;
a detector that detects X-rays having passed through the object and converts the detected X-rays into electric signals; and
an image processor that is configured to generate X-ray images of the object at the plurality of positions by reading out the electric signals, generate a virtual object from volume data of the object calculated by using the X-ray images of the object, and acquire virtual X-ray images of the virtual object of different energy bands by virtually emitting X-rays having different bands of energy spectrums to the generated virtual object.

15. The apparatus according to claim 14, wherein the image processor generates a multi-energy X-ray (MEX) image of the virtual object by using the acquired virtual X-ray images.

16. The apparatus according to claim 14, wherein the image processor acquires the virtual X-ray images captured at different positions by virtually emitting X-rays having the different bands of energy spectrums to the virtual object at the different positions.

17. The apparatus according to claim 16, wherein the image processor controls a generation of a stereoscopic image or a display of a stereoscopic image based on at least two virtual X-ray images of the virtual X-ray images captured at the different positions.

* * * * *